(12) United States Patent
Epstein et al.

(10) Patent No.: US 7,527,932 B2
(45) Date of Patent: May 5, 2009

(54) METHOD OF USING PHYSIOLOGICAL MARKERS TO ESTIMATE CARDIOVASCULAR RISK

(75) Inventors: Stephen E. Epstein, Rockville, MD (US); Juanhui Zhu, Potomac, MD (US)

(73) Assignee: MedStar Research Institute, Inc., Washington, DC (US)

( * ) Notice: Subject to any disclaimer, the term of this patent is extended or adjusted under 35 U.S.C. 154(b) by 0 days.

(21) Appl. No.: 10/495,081

(22) PCT Filed: Nov. 12, 2002

(86) PCT No.: PCT/US02/36227

§ 371 (c)(1), (2), (4) Date: Sep. 23, 2004

(87) PCT Pub. No.: WO03/039349

PCT Pub. Date: May 15, 2003

(65) Prior Publication Data

US 2005/0042678 A1 Feb. 24, 2005

Related U.S. Application Data

(60) Provisional application No. 60/331,189, filed on Nov. 9, 2001, provisional application No. 60/340,857, filed on Dec. 19, 2001, provisional application No. 60/394,245, filed on Jul. 9, 2002.

(51) Int. Cl.
G01N 33/53 (2006.01)
G01N 33/564 (2006.01)
C12Q 1/60 (2006.01)

(52) U.S. Cl. .................. 435/7.1; 435/7.21; 435/7.24; 435/7.8; 435/11; 436/506; 436/518; 436/536; 436/86; 436/87; 436/811

(58) Field of Classification Search .................. 435/5, 435/7.1, 7.21, 7.24, 7.32, 7.36, 7.8, 11; 436/518, 436/536, 811, 820, 506, 86, 87

See application file for complete search history.

(56) References Cited

U.S. PATENT DOCUMENTS 6,040,147 A 3/2000 Ridker et al.

OTHER PUBLICATIONS

Xu et al., Jul. 2000. Serum soluble heat shock protein 60 is elevated in subjects with atherosclerosis in a general population. Cicrulation 102 (1): 14-20.*
Burian et al., Mar. 2001. Independent and joint effects of antibodies to human heat-shock protein 60 and Chlamydia pneumoniae infection in the development of coronary atherosclerosis. Circulation 103 (11): 1503-1508.*
Kroll, Spring 2001. Infection as a cause of atherosclerosis. Journal of Clinical Ligand Assay 24 (1): 25-32.*
Füst et al., Sep. 2000. Lack of association between high levels of antibodies against 60 kD heat shock proteins and infection with Chl. pneumoniae and H. pylori in patients with coronary heart disease. Immunology Letters 73 (2-3): 139, Abs. #266.*
Hoppichler et al., 1996. Changes of serum antibodies to heat-shock protein 65 in coronary heart disease and acute myocardial infarction. Atherosclerosis 126: 333-338.*
Pockley et al., 2003. Serum heat shock protein 70 levels predict the development of atherosclerosis in subjects with established hypertension. Hypertension 42: 235-238.*
Burnett MS et al., "Atherosclerosis in apoE Knockout Mice Infected with Multiple Pathogens," J Infect Dis, 183(2):226-231 (2001).
Burnett MS et al., "Murine Cytomegalovirus Infection Increases Aortic Expression of Proatherosclerotic Genes," Circulation, 109(7):893-897 (2004).
Epstein SE et al., "Infection and Atherosclerosis: Potential Roles of Pathogen Burden and Molecular Mimicry," Arterioscler Thromb Vasc Biol, 20(6):1417-1420 (2000).
Epstein SE et al., "Potential Role of Cytomegalovirus in the Pathogenesis of Restenosis and Atherosclerosis," Am Heart J., 138(5 Pt 2):S476-478 (1999).
Epstein and Zhu "Lack of Association of Infectious Agents with Risk of Future Myocardial Infarction and Stroke: Definitive Evidence Disproving the Infection/Coronary Artery Disease Hypothesis?" Circulation, 100(13):1366-1368 (1999).
Epstein SE et al., "Infection and Atherosclerosis: Emerging Mechanistic Paradigms," Circulation, 100(4):e20-28 (1999).
Espinola-Klein C et al., "Impact of Infectious Burden on Extent and Long-term Prognosis of Atherosclerosis," Circulation, 105:15-21 (2002).
Espinola-Klein C et al., "Impact of Infectious Burden on Progression of Carotid Atherosclerosis," Stroke, 33:2581-2586 (2002).
Horne BD et al., "Greater Pathogen Burden But Not Elevated C-reactive Protein Increases the Risk of Clinical Restenosis After Percutaneous Coronary Intervention," Am Heart J, 144:491-500 (2002).
Huittinen T et al., "Autoimmunity to Human Heat Shock Protein 60, Chlamydia Pneumoniae Infection, and Inflammation in Predicting Coronary Risk," Arterioscler Thromb Vasc Biol, 22(3):431-437 (2002).
Libby P et al., "Novel Inflammatory Markers of Coronary Risk: Theory Versus Practice," Circulation, 100(11):1148-1150 (1999).

(Continued)

Primary Examiner—James L Grun
(74) Attorney, Agent, or Firm—Wolf, Greenfield & Sacks, P.C.

(57) ABSTRACT

An individual's risk profile for developing a cardiovascular disorder or for experiencing a cardiovascular event is determined by 1) measuring levels of certain stress-evoked proteins including heat shock proteins (HSPs), cytokines, adhesion molecules, chemokines, and the like, or titers of the antibodies targeted to them, or 2) determining the number of seropositive responses to a group of pathogens that have been associated with the presence of atherosclerosis and/or clinical events related to atherosclerosis. The measured levels are compared with clinically derived standards that define the association of these markers with cardiovascular disease. These markers are independent of traditionally recognized risk factors.

5 Claims, 6 Drawing Sheets

OTHER PUBLICATIONS

Mayr M et al., "Infections, Immunity, and Atherosclerosis: Associations of Antibodies to Chlamydia Pneumoniae, Helicobacter Pylori, and Cytomegalovirus with Immune Reactions to Heat-shock Protein 60 and Carotid of Femoral Atherosclerosis," Circulation, 102(8):833-839 (2000).

Mayr M et al., "Endothelial Cytotoxicity Mediated by Serum Antibodies to Heat Shock Proteins of *Escherichia coli* and *Chlamydia pneumoniae*: Immune Reactions to Heat Shock Proteins as a Possible Link Between Infection and Atherosclerosis," Circulation, 99(12):1560-1566 (1999).

Pasceri V et al., "Association of Virulent Helicobacter Pylori Strains with Ischemic Heart Disease," Circulation, 97(17):1675-1679 (1998).

Pockley AG et al., "Circulating Heat Shock Protein 60 is Associated with Early Cardiovascular Disease," Hypertension, 36(2):303-307 (2000).

Prasad A et al., "Predisposition to Atherosclerosis by Infections: Role of endothelial Dysfunction," Circulation, 106(2):184-190 (2002).

Rott D et al., "Serum of Cytomegalovirus-infected Mice Induces Monocyte Chemoattractant Protein-1 Expression by Endothelial Cells," J Infect Dis, 184(9):1109-1113 (2001).

Rupprecht HJ et al., "Impact of Viral and Bacterial Infectious Burden on Long-Term Prognosis in Patients with Coronary Artery Disease," Circulation, 104:25-31 (2001).

Smieja M et al., "Multiple Infections and Subsequent Cardiovascular Events in the Heart Outcomes Prevention Evaluation (HOPE) Study," Circulation, 107:251-257 (2003).

Wright BH et al., "Elevated Levels of Circulating Heat Shock Protein 70 (Hsp70) in Peripheral and Renal Vascular Disease," Heart Vessels, 15(1):18-22 (2000).

Xu Q et al., "Association of Serum Antibodies to Heat-Shock Protein 65 with Carotid Atherosclerosis," Lancet, 341(8840):255-259 (1993).

Xu Q et al., "Association of Serum Antibodies to Heat-Shock Protein 65 with Carotid Atherosclerosis: Clinical Significance Determined in a Follow-up Study," Circulation, 100(11):1169-1174 (1999).

Zhu J et al., "Association of Serum Antibodies to Heat-Shock Protein 65 with Coronary Calcification Levels: Suggestion of Pathogen-Triggered Autoimmunity in Early Atherosclerosis," Circulation, 109(1):36-41 (2004).

Zhu J et al., "Lack of Association of Helicobacter Pylori Infection with Coronary Artery Disease and Frequency of Acute Myocardial Infarction or Death," Am J Cardiol, 89(2):155-158 (2002).

Zhu J et al., "Increased Serum Levels of Heat Shock Protein 70 are Associated with Low Risk of Coronary Artery Disease," Arterioscler Thromb Vasc Biol, 23(6):1055-1059 (2003).

Zhu J et al., "Cytomegalovirus in the Pathogenesis of Atherosclerosis: The Role of Inflammation as Reflected by Elevated C-reactive Protein Levels," J Am Coll Cardiol, 34(6):1738-1743 (1999).

Zhu J et al., "The Possible Role of Hepatitis A Virus in the Pathogenesis of Atherosclerosis," J Infect Dis, 182(6):1583-1587 (2000).

Zhu J et al., "Host Response to Cytomegalovirus Infection as a Determinant of Susceptibility to Coronary Artery Disease: Sex-based Differences in Inflammation and Type of Immune Response," Ciriculation, 102(20):2491-2496 (2000).

Zhu J et al., "Effects of Total Pathogen Burden on Coronary Artery Disease Risk and C-reactive Protein Levels," Am J Cardiol, 85(2):140-146 (2000).

Zhu J et al., "Discordant Cellular and Humoral Immune Responses to Cytomegalovirus Infection in Healthy Blood Donors: Existence of a Th1-type Dominant Response," Int Immunol, 13(6):785-790 (2001).

Zhu J et al., "Prospective Study of Pathogen Burden and Risk of Myocardial Infarction or Death," Circulation, 103(1):45-51 (2001).

Zhu J et al., "Antibodies to Human Heat-Shock Protein 60 are Associated with the Presence and Severity of Coronary Artery Disease: Evidence for an Autoimmune Component of Atherogenesis," Circulation, 103(8):1071-1075 (2001).

* cited by examiner

METHOD OF USING PHYSIOLOGICAL MARKERS TO ESTIMATE CARDIOVASCULAR RISK

RELATIONSHIP TO OTHER APPLICATIONS

This application claims the benefit of U.S. Provisional Application Ser. No. 60/331,189, filed Nov. 09, 2001, and of U.S. Provisional Application Ser. No. 60/340,857, filed Dec. 19, 2001, and of U.S. Provisional Application Ser. No. 60/394,245, filed Jul. 09, 2002. The entire disclosure of each of the above-identified U.S. Provisional Patent Applications is incorporated herein by reference.

BACKGROUND OF THE INVENTION

1. Field of the Invention

This invention relates to diagnostic tests for characterizing an individual's risk developing a disease and more particularly to tests for determining risk of developing atherosclerotic diseases such as myocardial infarction, angina pectoris, stroke, and peripheral vascular disease.

2. Brief Description of the Prior Art

Almost 60 million Americans have one or another form of cardiovascular disease. Approximately 7 million Americans are alive having survived a heart attack, with over one million additional Americans expected to experience heart attacks each year. Over 6 million Americans have chest pain (angina pectoris) caused by coronary heart disease, and nearly 5 million have congestive heart failure. Approximately 2.5 million patients undergo angioplasty or bypass surgery procedures each year. Thus, cardiovascular disease is highly prevalent in the United States, as well as in all other industrialized nations and, despite new and improved therapies, in these countries this group of disease continues to be the single most frequent cause of morbidity and mortality. As a result, identification of individuals at risk of developing cardiovascular disease is a critical strategy to more effectively prevent and/or treatment these diseases.

Several risk factors predicting cardiovascular events which can be measured from blood samples are now being used clinically, such as those relating to LDL and HDL cholesterol levels. However, many patients with arteriosclerosis do not exhibit such risk factors. Moreover, moreover, cardiovascular events occur even in many individuals who do not demonstrate such risk factors and thus are considered to be at low risk of experiencing a cardiovascular event.

Accordingly, a need has continued to exist for methods of detecting risk of a patient developing cardiovascular disease.

SUMMARY OF THE INVENTION

This need has now been met by the method of this invention wherein an individual's risk profile of developing a future cardiovascular disorder is determined by 1) measuring levels of certain stress-evoked proteins, including heat shock proteins (HSPs), cytokines, adhesion molecules, chemokines, and the like, or titers of the antibodies targeted to them, or 2) determining the number of seropositive responses to a group of pathogens that have been associated with the presence of atherosclerosis and/or clinical events related to atherosclerosis. These new tests help predict, for example, the risk of an individual developing atherosclerosic diseases such as myocardial infarction, angina pectoris, stroke, and peripheral vascular disease (including claudication and gangrene). The basis of these new tests derive from the critical importance of HSPs in cellular function, and the significant role which infection plays in contributing to the onset of atherosclerosis.

Consequently this invention comprises a method for characterizing an individual's risk profile of developing a future myocardial infarction, or of developing angina, or of developing claudication or gangrene, comprising obtaining a level of a marker (which could be a molecule or antibody targeted to a molecule) that conveys information as to the susceptibility or resistance to the development of atherosclerosis, comparing the level of the marker to a predetermined value, and characterizing the individual's risk profile of developing a cardiovascular condition such as myocardial infarction, or angina, or stroke, or claudication or gangrene, based upon the level of the marker in comparison to the predetermined value. The marker chosen is one that normally plays an important protective role in the responses to stress of cells of the individual, but one which could also serve as an antigen triggering autoimmune responses that could exacerbate the atherosclerosis process.

Accordingly, it is an object of the invention to provide a method for characterizing the risk profile of an individual for developing cardiovascular disease.

A further object it to provide a method for characterizing the risk profile of an individual for experiencing a clinical symptom of cardiovascular disease.

A further object is to provide a method for characterizing the risk profile of an individual as a means of predicting the possibility of a cardiovascular condition such as myocardial infarction, or angina, or stroke, or claudication or gangrene.

Further objects of the invention will be apparent from the description of the invention which follows.

DETAILED DESCRIPTION OF THE INVENTION AND PREFERRED EMBODIMENTS

This invention is based on the discovery that certain substances found in the blood of an individual can serve as markers for demonstrating a potential for development of cardiovascular disease, e.g., athersclerosis, and clinical manifestations thereof, such as myocardial infarction, angina, stroke, or peripheral vascular conditions due to diminished blood supply, such as claudication or gangrene.

These markers, and their concentration, can be detected in the plasma of individuals using conventional modern analytical methods. Consequently, correlations can be established by conventional clinical studies between the plasma levels of these markers and the prevalence of various cardiovascular conditions and/or diseases in human patients. A scale can then be established associating the plasma levels of the markers or combinations thereof with the risk of developing such cardiovascular conditions and/or diseases. Such a scale or standard can then be used to determine the risk profile of an individual for developing or experiencing such a condition or disease. This is accomplished by measuring the patient's plasma levels for one or more of the established markers, and comparing the measured levels with the established scale or standard, so as to arrive at the risk profile.

As indicated above, the markers of cardiovascular risk that are used in the method of the invention include
  a) the plasma level of a stress-evoked protein,
  b) the plasma titer of an antibody to a stress-evoked protein, and
  c) the number of seropositive responses to pathogens associated with the presence of atherosclerosis or clinical events related thereto.

It should be noted that the correlation between the plasma level of a marker and the risk of future cardiovascular condition or disease may be either positive or negative. That is, certain markers may indicate an increased risk of future cardiovascular problems, and other markers may indicate decrease risk.

The application of the method of the invention using the above-listed markers is discussed in more detail below.

Heat Shock Proteins

Heat Shock Proteins (HSPs), which consist of a large family of proteins that share high homolgy among species, are present in all cells and have several functions. These include the assembly of newly synthesized intracellular proteins, their transport across cell membranes, and the removal of denatured proteins. These and other functions convey to HSPs critically important roles in cellular repair following injury, and in protecting the cell against a broad range of stresses, which include heat shock (from which their name derives), toxins, oxidative stress, inflammation, sepsis, and ischemia-induced injury. Although the protective role of HSPs in a cell's response to acute stress is well established, evidence has emerged indicating that some of the HSPs contribute to the development of chronic disease, and that this most likely occurs through autoimmune responses.

Consequently, any of the heat shock proteins may be useful as a marker for assessing the cardiovascular health and/or risk of a patient. According to the invention, one determines whether a particular heat shock protein is correlated, positively or negatively, with the prevalence of coronary artery disease or other cardiovascular disease, and then uses the measured levels of a selected heat shock protein to evaluate the cardiovascular status of a patient. Accordingly, the invention includes the use of any heat shock protein exhibiting a correlation with cardiovascular status as a marker for evaluating the cardiovascular health of a patient, either alone or in combination with other indicators of a cardiovascular risk, as discussed below. Similarly, antibodies to any heat shock proteins that have been demonstrated to have a positive correlation with the existence of cardiovascular disease can be used as a marker to evaluate the cardiovascular health and/or risk of a patient, as discussed more fully below.

The functions of the ubiquitous HSP intracellular molecules have been outlined above. HSP70 is one of the more extensively studied HSPs. With stress, HSP70 translocates to the nucleus and associates with nucleoli. It shares in many of the above HSP functions and, in addition, protects against myocardial ischemic injury. Thus, it is increased in the heart in response to prolonged ischemia, and early studies demonstrated that prior whole body exposure to heat, which results in increased levels of HSP70, improves recovery of rat and of rabbit hearts from ischemic-induced injury. More specific studies on the role of HSP70 demonstrated that overexpression of HSP70 protects an embryonic cardiac cell line from hypoxic injury, and that the hearts of transgenic mice overexpressing HSP70 are more resistant to ischemic injury.

Figure 1:
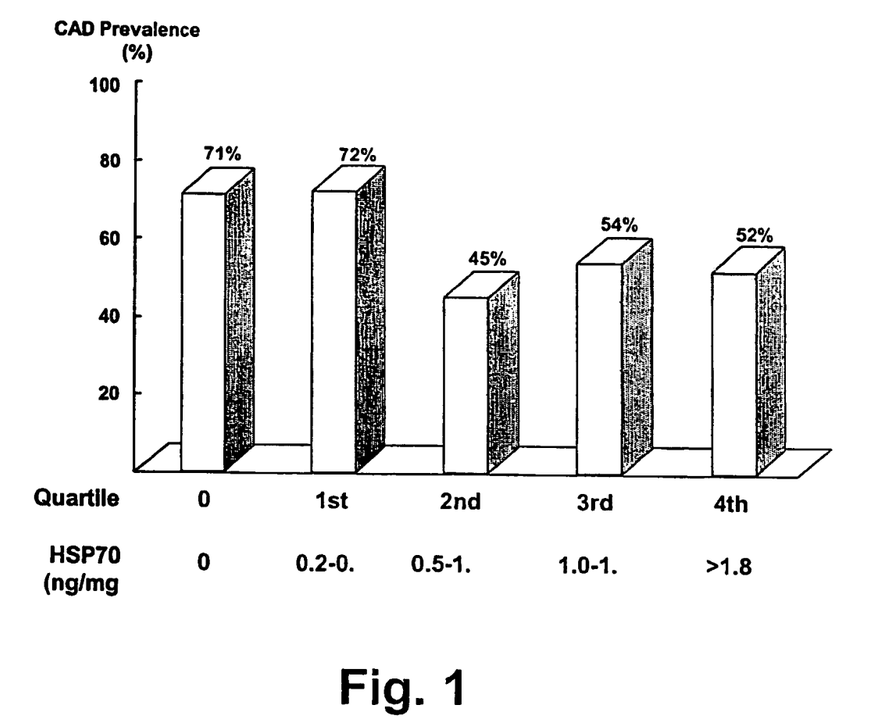
FIG. 1 is a graph showing the relation between CAD prevalence and serum levels of HSP70.

Most important to this invention are the data the inventors recently obtained in a clinical study of patients with CAD. We found that serum HSP70 was detectable in 67% of study subjects, and, most importantly, that elevated serum levels of HSP70 negatively correlated with the prevalence of coronary artery disease (CAD) (P=0.015). On multivariate logistical regression analysis, individuals with HSP70 levels above the median (0.5 ng/ml) had half the risk of CAD than individuals with levels below the medium, an association independent of traditional CAD risk factors (P=0.011). Table 1 presents data showing the percentiles of serum levels of HSP70 levels and risk ratio for the presence of CAD. The data show that there is a consistent reduction in risk ratio, adjusted for usual CAD confounding variables, at levels of HSP70 of 0.5 ng/ml or higher. The risk reduction ranges from 45 to nearly 70%. FIG. 1 shows that HSP plasma levels above the median (0.5 ng/ml) were associated with a lower prevalence of CAD. A threshold value of 0.5 ng/ml appears to convey maximal benefit. Disease severity (number diseased vessels) was also inversely associated with HSP70 levels (P=0.011).

TABLE 1

| Cut off percentile | HSP70 ng/ml | CAD (%) | No CAD (%) | RR | 95% CI | Adjusted RR (95% CI) |
|---|---|---|---|---|---|---|
| $25^{th}$ | >0.50 | 107/206 (52) | 104/144 (72) | 0.42 | 0.26-0.66 | 0.55 (0.32-0.94) |
| $50^{th}$ | >0.98 | 75/174 (43) | 66/106 (62) | 0.46 | 0.28-0.75 | 0.57 (0.32-1.02) |
| $75^{th}$ | >1.82 | 37/136 (27) | 34/74 (46) | 0.44 | 0.24-0.79 | 0.44 (0.22-0.89) |
| $90^{th}$ | >3.44 | 14/133 (12) | 15/55 (27) | 0.38 | 0.17-0.85 | 0.32 (0.12-0.87) |

An interesting and unexpected finding of this investigation was that HSP70 levels negatively correlated with cytomegalovirus (CMV) infection. The relation between increasing HSP70 levels and decreasing prevalence of CMV seropositivity remained significant after adjustment for CAD risk factors and seropositivities to other infectious pathogens (P=0.0086). This inverse relationship is compatible with the concept that HSP70 conveys protection against CMV infection, a conclusion congruous with other studies demonstrating that certain viruses, including CMV, induce HSP70 expression upon infection, and that HSP70 is the mediator responsible for the potent antiviral activity of certain prostaglandins (PGs), such as PGAs and PGJs, against a wide variety of viruses. This finding takes on added significance when it is consideredthat several viruses, such as CMV, HAV, HSV1, and HSV2 have been identified as playing a role in atherogenesis.

Figure 2:
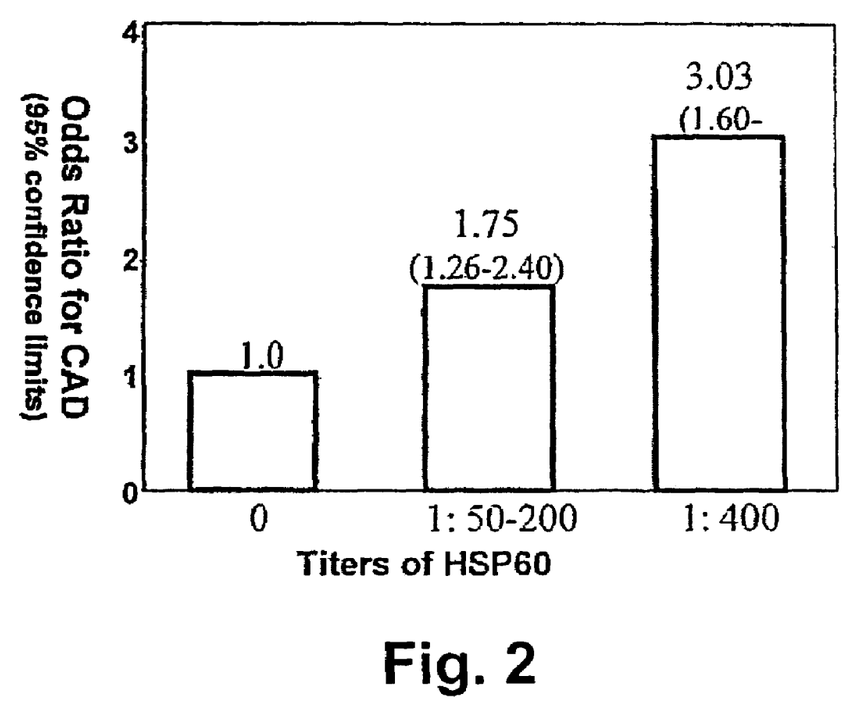
FIG. 2 is a graph showing the odds ratio for CAD versus heat shock protein (HSP) 60 antibody titers.
Figure 3:
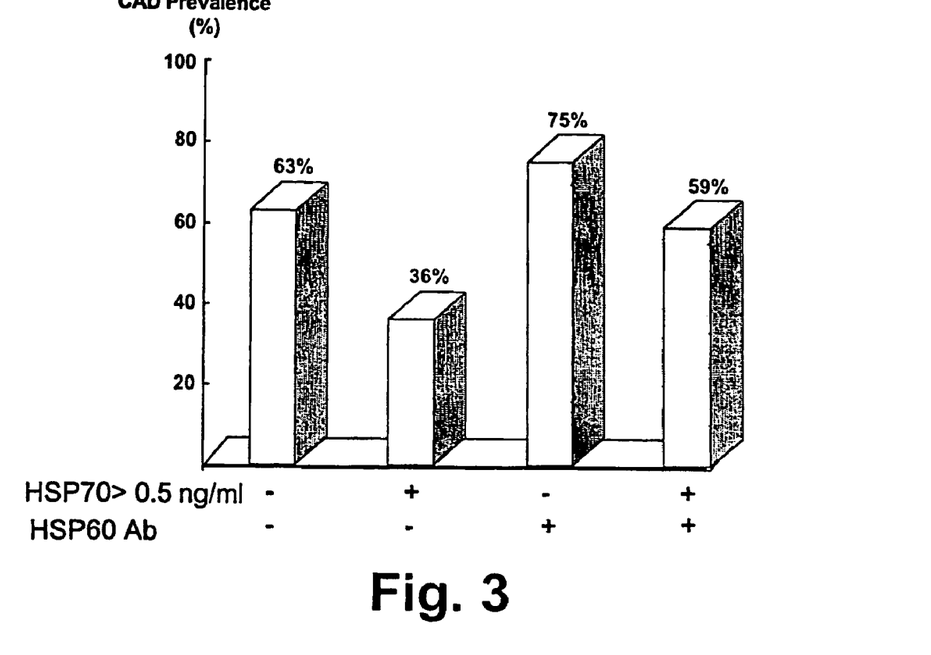
FIG. 3 is a graph showing the relation between serum levels of HSP70 and antibodies to HSP60 with respect to CAD prevalence.

Although the protective role of HSPs in a cell's response to acute stress is well established, it has been demonstrated that certain HSPs contribute to the development of chronic disease, and that this probably occurs through autoimmune responses. Thus, HSP60, a mitochondrial HSP, appears to serve as an autoantigen and contributes to such human diseases as rheumatoid arthritis, insulin-dependent diabetes mellitus, and atherosclerosis. In regard to atherosclerosis, The inventors have recently demonstrated that antibodies targeted to HSP60 correlate with the presence and extent of CAD as shown in FIG. 2. FIG. 3 shows the interaction between serum levels of HSP70 and antibodies to HSP60 on CAD prevalence. Increasing serum levels of HSP70 are protective, while the presence of antibodies to HSP60 convey added risk of having CAD. The two middle bars are most informative. The presence of "protective" HSP70 protein in the serum, in the absence of antibodies to HSP60, is associated with a CAD risk of only 36%. In contrast, the presence of antibodies to HSP60, in the absence of HSP70 protein in the serum, is associated with a CAD risk of 75%.

The triggers of the postulated autoimmune response involved in atherogenesis are largely conjectural. Infection, however, is one of the leading candidates. Bacteria appear to express HSPs that are homologous to human HSP, and viruses, although they do not express HSPs, do incorporate host HSP into their cellular membranes as they leave the host cell in the course of their infectious cycles. It has been thus postulated that infection induces the development of antibodies targeted to the HSPs carried by pathogens, but which cross-react with human HSP that is overexpressed on endothelial cells. The results of several studies have been compatible with this concept, and demonstrated an association between antibodies to mycobacterial HSP65 (a bacterial homologue of human HSP60) and carotid artery thickening.

The inventors recently examined the hypothesis that there is a pathogen-triggered autoimmunity targeted to HSP in early atherosclerosis. In testing the validity of the hypothesis, a group of healthy asymptomatic individuals who were undergoing screening for CAD by electron beam computed tomographic imaging (EBCT) of the coronary arteries was identified. The experiment examined whether there was an association between elevated coronary calcification and the presence of pathogen derived HSP. The screening was conducted for a standard pathogen HSP—myocobacterial HSP65. Serum specimens from 201 healthy asymptomatic subjects undergoing electron beam computed tomographic imaging were evaluated. It was found that 84% of the study subjects had anti-mHSP65 IgG antibodies. Mean titers of mHSP65 antibodies were higher (1:394 vs. 1:267, P=0.012) in individuals with, than in those without, elevated levels of coronary calcium. Increasing titers of mHSP65 antibodies were significantly associated, in a dose-response manner, with elevated levels of coronary calcification after multivariate adjustment (P=0.037). Individuals with the highest titers of mHSP65 antibodies (1:800) had an adjusted odds ratio (OR) of 11.3 for having elevated coronary calcium.

It should be emphasized that the predictive value of serum levels of HSP70, or of antibody titers to HSP65 and to mHSP65 creates an inference as to the susceptibility or resistance to the development of atherosclerosis that is independent of other established CAD risk factors. Importantly, these risk predictors are additive with risk factors derived from total cholesterol levels and from C-reactive protein (CRP) levels. Thus, the level of HSP70, or of antibody titers to HSP65 or to mHSP65, do not simply duplicate that which is measured when levels of cholesterol are measured.

As mentioned above, these discoveries have led to new diagnostic tests. Thus, the test provides for characterizing an individual's risk profile of developing atherosclerotic diseases such as myocardial infarction, angina pectoris, stroke, and peripheral vascular disease (including claudication and gangrene). The method consists of measuring the level of a marker (which could be a molecule or antibody targeted to a molecule) that conveys information as to the susceptibility or resistance to the development of atherosclerosis is selected from the group consisting of HSP70, HSP65, and mHSP65. For example, the level of serum HSP70 is determined and then compared to a predetermined value, and the individual's risk profile of developing future atherosclerotic diseases such as myocardial infarction, angina pectoris, stroke, and peripheral vascular disease is determined. The predetermined value may be a single value, a plurality of values, a single range or a plurality of ranges. In one embodiment, the predetermined value is a plurality of predetermined-marker level ranges and the comparing step involves determining in which of the predetermined marker level ranges the individual's level falls (see FIG. 1).

According to yet another aspect of the invention, a method is provided in which the level of HSP70 is combined-with that of antibody titers to HSP65 and/or to antibody titers to mHSP65 so that an aggregate number reflecting the susceptibility or resistance to the development of atherosclerotic diseases. Still another embodiment of the invention is to combine the risk information conveyed by levels of HSP70, by antibody titers to HSP65 alone, by antibody titers to HSP65, alone or in combination, to the risk number conveyed when these are used together with traditional risk factors, such as cholesterol levels and/or CRP levels. Thus, an estimate of the HSP markers' contribution to risk is obtained. The level of the marker is compared to a predetermined value to establish a first risk value. A level of a cholesterol or CRP in the individual also is obtained. The level of the cholesterol or CRP in the individual is compared to a second predetermined value to establish a second risk value. The individual's risk profile of developing the cardiovascular disorder then is characterized based upon the combination of the first risk value and the second risk value, wherein the combination of the first risk value and second risk value establishes a third risk value different from the first and second risk values. In particularly important embodiments, the third risk value is greater than either of the first and second risk values.

In addition to the heat shock proteins discussed above, other stress-evoked proteins may be generated by the organism in response to stresses as enumerated above, including heat shock, toxins, oxidative stress, inflammation, sepsis, and ischemia-induced injury, and the like. These stress-evoked proteins can also be used, individually or in combination with each other and/or the level of HSPs, as markers for developing a risk profile for patients with regard to development of coronary artery disease (CAD), atherosclerosis, or experience of an adverse event relating to the course of such disease, e.g., myocardial infarction in cardiovascular disease or claudication and gangrene, as related to peripheral artery disease. Such stress-evoked proteins are produced by cells when challenged by unfavorable physiological conditions, as discussed above, such as inflammation or infection (which may also elicit an inflammatory response). These stress-evoked proteins include cytokines and their receptors, adhesion molecules and their receptors, and chemokines and their receptors. These proteins are well-recognized and are identified by standard terminology in the art. They can be detected and quantitated by conventional techniques. Accordingly, in addition to heat shock proteins the following stress-evoked proteins can be used as markers in developing a risk profile of a patient.

Cytokines, such as, but not limited to, IL6, IL10, IL18, and interferon gamma (IFNγ) and their receptors.

Adhesion molecules, such as, but not limited to, ICAM, VCAM, and their receptors.

Chemokines, such as, but not limited to, MCP-1 and its receptor CCR2.

The procedures for establishing correlations between the plasma levels of these stress-evoked proteins are analogous to those used with HSPs.

If antibodies are generated to stress-evoked proteins, the presence of such antibodies may also be used as markers for generating cardiovascular risk profiles. Any HSPs, cytokines, adhesion molecules, and chemokines, as well as molecules related to their presence, such as receptors and/or antibodies may be used as markers for risk profiling according to the invention. The above-listed molecules are merely representative of the groups. The skilled practitioner can select an appropriate molecule or group of molecules from among this class of stress-evoked proteins.

The invention also contemplates kits comprising assays for measuring levels of markers (which could be a molecule or antibody targeted to a molecule) that conveys information as to the susceptibility or resistance to the development of atherosclerosis selected from the group consisting of HSP70, HSP65, and mHSP65, as well as the other markers of cardiovascular risk discussed above.

Pathogen Burden

Accumulating evidence indicates that infection predisposes to the development of atherosclerosis, and several pathogens have been associated with atherosclerosis. The inventors reasoned that if infection is causally related to atherosclerosis, it would be unlikely that a single agent plays a unique role. Rather, it was considered that multiple infectious agents contribute to atherosclerosis, and hypothesized that the risk of cardiovascular disease posed by infection is related to the number of pathogens with which an individual has been exposed (the 'pathogen burden'). that hypothesis was first evaluated in a group of individuals being evaluated for CAD. It was found that CAD risk increased significantly in relation to pathogen burden. A second present prospective study with a different patient cohort, demonstrated that risk of myocardial infarction (MI) or death among CAD patients increases as pathogen burden increases. Moreover, we found that pathogen burden was a risk factor for CAD and for MI or death independent of traditional risk factors, including CRP levels.

Role of Infection in Atheroslerosis and Risk Prediction by Pathogen Burden

As many as 50% of patients with atherosclerosis lack currently identified risk factors. Inflammation is an essential component of atherogenesis, and infection is one of the candidate inflammatory triggers. Compatible with this is the demonstration that infection of apoE knockout mice with CMV or with *C. pneumoniae* exacerbates atherosclerotic lesion development.

In addition, multiple studies suggest that the mechanisms by which infection contributes to atherosclerosis can derive from the direct effects of the pathogen infecting the vessel wall, with different laboratories implicating one or another pathogen as the causal agent. Additional evidence indicates that mechanisms other than those deriving from direct infection of the vessel wall also plays a role in atherogenesis. These mechanisms include exposure of the vessel wall to circulating cytokines, inflammatory cells, antibodies targeted to self proteins, and autoagressive T-cells.

Figure 4:
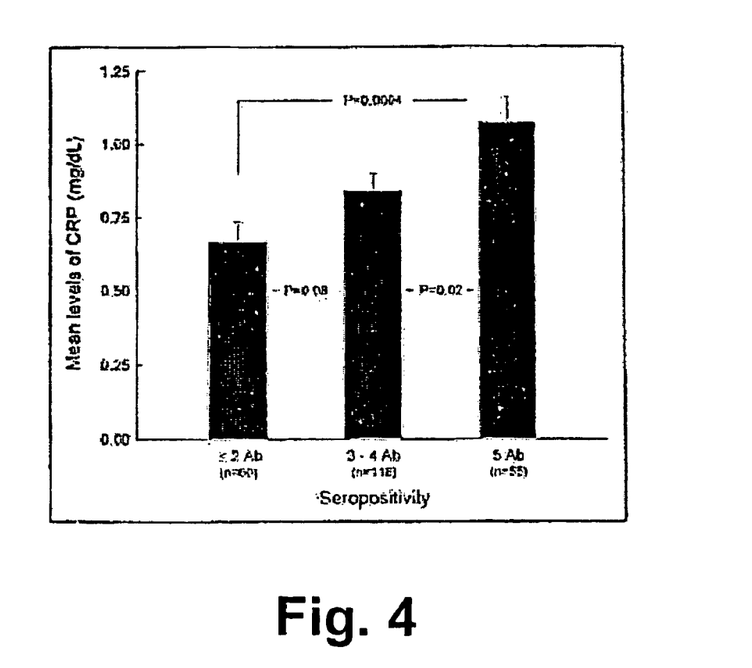
FIG. 4 is a graph showing the association between numbers of pathogens to which individuals were exposed and mean levels of CRP (mg/dl with SE).

In studies dedicated to the evaluation of individual pathogens, several pathogens were associated with the development of atherosclerosis. The inventors reasoned that if infection plays a role in atherogenesis, it would be highly likely that multiple pathogens would be causally involved and, importantly, that CAD risk would relate to the aggregate pathogen load (herein termed pathogen burden). This hypothesis was tested in a group of individuals being evaluated for CAD by coronary angiography. The relationship of pathogen burden (aggregate number of a panel of five pathogens to which an individual had been exposed, as determined by seropositivity) to CRP levels (an index of inflammation) and to CAD risk was determined. The pathogens tested were CMV, Chlamydia, hepatitis A virus, HSV-1 and HSV-2. A dose-response relationship was found. As the number of seropositive responses an individual had increased, there was an increase in CRP levels and in CAD prevalence as shown in FIG. 4, which presents the Association between numbers of pathogens to which individuals were exposed (as reflected by seropositivity) and mean levels of CRP (mg/dl with SE). Mean values of CRP were $0.67\pm0.07$ mg/dl in patients exposed to $\leq2$ pathogens, $0.84\pm0.06$ mg/dl in patients exposed to 3 or 4 pathogens, and $1.08\pm0.09$ mg/dl in patients exposed to 5 pathogens. Overall linear trend achieves significance ($p=0.001$). (In the figure legend Ab=antibody.)

Figure 5:
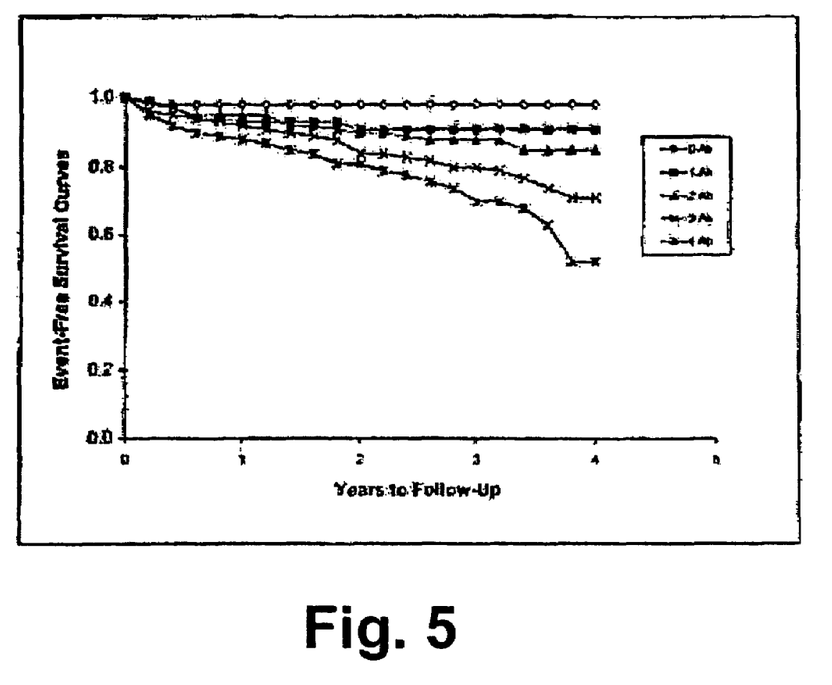
FIG. 5 is a graph showing the MI of death-free survival curves according to pathogen burden.

These results were expanded in a prospective study; pathogen burden was directly related to the event rate (myocardial infarction (MI) and death) in a cohort of patients with angiographically documented CAD—the greater the number of seropositive responses, the greater the event rate as shown in FIG. 5, which shows the MI of death-free survival curves according to pathogen burden (number of positive IgG antibodies). Pathogen burden was based on seropositivity to the four pathogens: CMV, HAV, HSV 1 and HSV2. In the figure legend Ab=antibody.)

It therefore appears that the risk for CAD and CAD event rate are related to the aggregate number of potentially atherogenic pathogens to which an individual has been exposed.

Accordingly, the pathogen burden includes the effects of any pathogen that is shown to produce atherogenic effects, either by direct infection of the vessel wall or by reason of exposure of the vessel wall to humoral factors or cells generated by the body's reaction to infection of the blood vessels or other organs. Consequently, according to the invention, any infectious challenge to the body by any pathogenic agent, including but not limited to viruses, bacteria, fungi, parasites, and the like, is included in the pathogenic burden.

Figure 6:
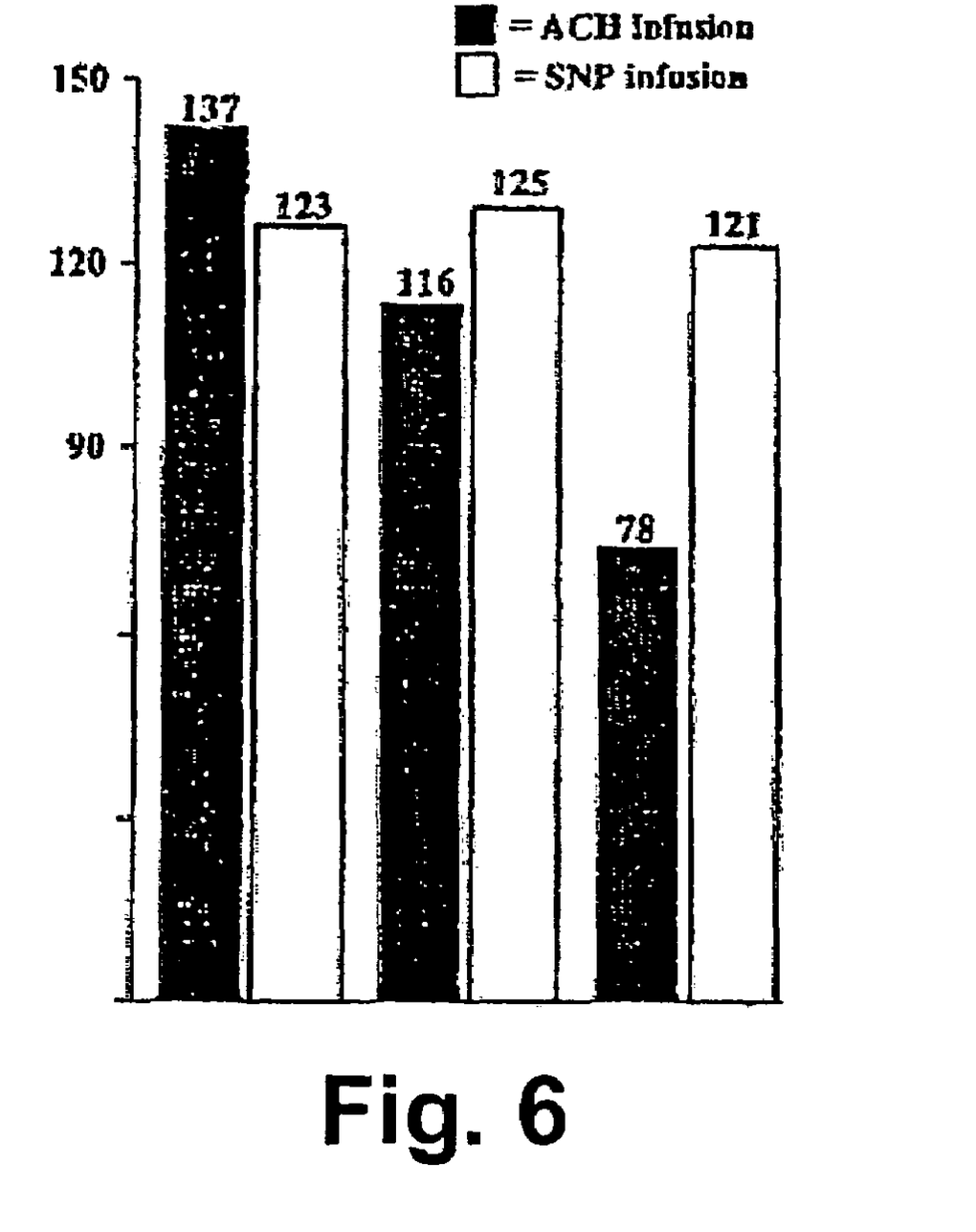
FIG. 6 is a graph showing the effect of pathogen burden on endothelial dysfunction.

The role of pathogen burden in atherogenesis was further indicated by a recently completed study in which the inventors found that pathogen burden was related to progressive deterioration in endothelial function. The study tested for the presence of endothelial dysfunction (one of the earliest functional abnormalities in atherosclerosis) in the coronary arteries of 231 individuals (85 with normal coronaries (NCA) and 126 with CAD). Endothelium-dependent and independent vasodilation was tested with intracoronary acetylcholine (ACH, 30 µg/min) and sodium nitroprusside (SNP, 40 µg/min), respectively, and flow reserve with adenosine (ADO, 2.2 mg/min). Blood flow velocity was measured using a Doppler wire. The study found progressive deterioration in endothelial function (ACH-response), but not SNP or ADO responses, with increasing exposure to pathogens; patients with 4 or 5 past infections had depressed ACH responses vs. the 0-1 infection group, as shown in FIG. 6 which summarizes the effect of pathogen burden on endothelial dysfunction. Endothelium-dependent vasodilation is determined by intracoronary infusion of acetylcholine (ACH); endotheliumindependent vasodilation by infusion of sodium nitroprusside (SNP). The results demonstrate that there is a direct relation between pathogen burden and impairment of endothelium-dependent vasodilation, whereas endotheliumindependent vasodilation is intact regardless of pathogen burden.

The number of past infections predicted ΔFlow ($p<0.003$) in response to ACH, independent of age, gender, CAD, body mass index, serum cholesterol, hypertension, diabetes, and smoking history. ACH response was also depressed in the NCA subgroup; (ΔFlow with ACH 185% vs. 79%, $p=0.004$, in 0-1 vs. 4-5 infection groups). Thus, pathogen burden is a risk factor for coronary endothelial dysfunction, further supporting a pathophysiological role of infection in CAD.

Individual Variations in Host Pathogen Interactions

Figure 7:
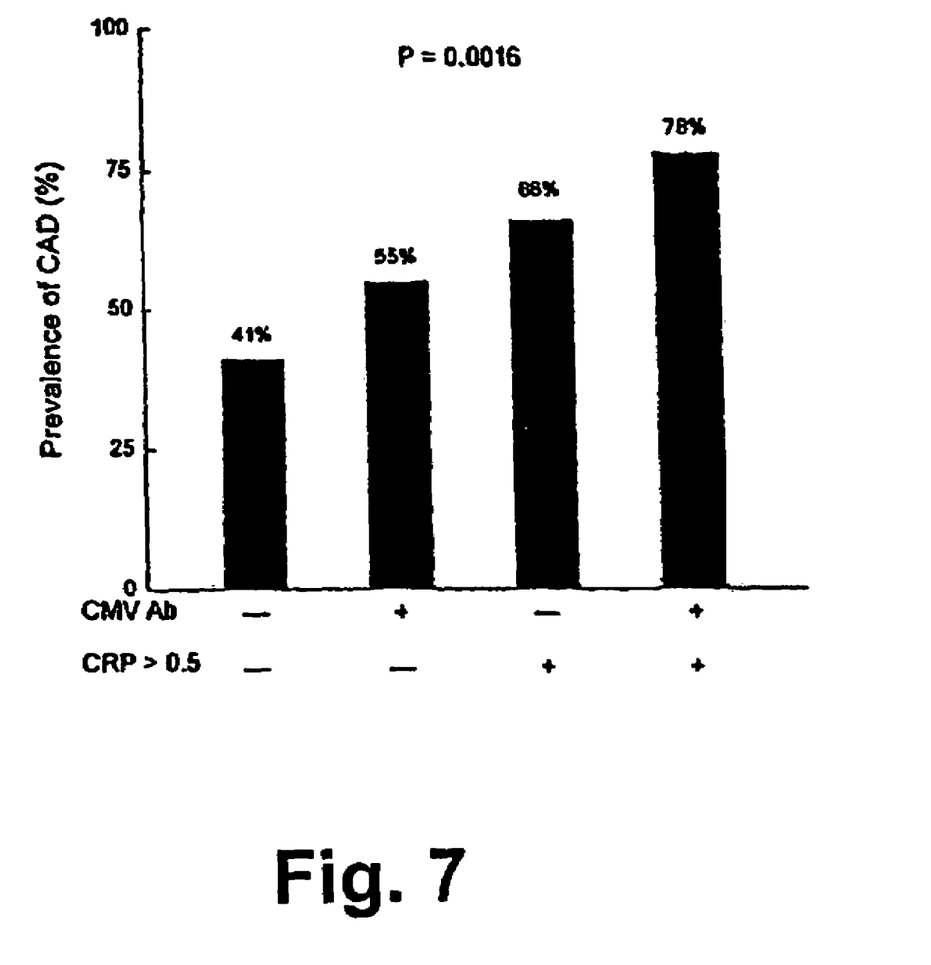
FIG. 7 is a graph showing the prevalence of CAD among subgroups with variation in inflammation and CMV infection.

Although many epidemiologic studies have demonstrated that seropositivity to several infectious agents is associated with increased CAD risk, the data are inconsistent, with other studies showing no increased risk. One possible explanation for this disparity is that prior infection, as reflected by seropositivity, contributes to CAD risk depends, at least in part, on the capacity of the host to suppress pathogen inflammatory activity. The validity of this concept was suggested by a study in which the inventors demonstrated that 1) while some individuals seropositive to CMV have elevated CRP levels, in others CRP is within the normal range, and 2) highest CAD prevalence occurs in the subgroup with combined CMV seropositivity and elevated CRP levels, as shown in FIG. 7, which shows the prevalence of CAD among subgroups with variation in inflammation and CMV infection. When adjustment for CAD risk factors, the odds ratios for CAD were 1.3(95% CI, 0.4 to 4.4; P=0.7) in the subgroup with CMV seropositivity alone, 2.3 (95% CI, 0.7 to 7.5; P=0.2) in the subgroup with elevated CRP levels alone, and 4.3 (95% Cl, 1.4 to 13.1; P=0.01) in the subgroup with combined CMV seropositivity and elevated CRP levels. Overall linear trend achieves significance even after adjustment for CAD risk factors (P=0.0016). CMV Ab+ or CMV Ab−: CMV antibody response positive or negative, respectively; CRP>0.5+ or CRP>0.5−: CRP levels>0.5 mg/dL or CRP levels<0.5 mg/dL, respectively.

When adjusted for CAD risk factors, the odds ratios for CAD were 1.3 in the subgroup with CMV seropositivity alone (P=0.7), 2.3 in the subgroup with elevated CRP levels alone (P=0.2), and 4.3 in the subgroup with combined CMV seropositivity and elevated CRP levels (P=0.01).

Consequently, the invention also comprises a method for characterizing an individual's risk profile of developing a future myocardial infarction, or of developing angina, or of developing claudication or gangrene, comprising determining the number of seropositive responses to a group of pathogens (pathogen burden) that have been associated with the presence of atherosclerosis and/or clinical events related to atherosclerosis, comparing the risk of atherosclerosis and/or clinical events related to atherosclerosis to the risk present if the pathogen burden is none or one, and characterizing the individual's risk profile of developing a future myocardial infarction, or of developing angina, or of developing a stroke, or of developing claudication or gangrene based upon the level of the marker in comparison to the predetermined value. The marker may be selected from the group including, but not limited to, cytomegalovirus (CMV), hepatitis A virus (HAV), herpes simplex virus type 1 (HSV 1), HSV type 2 (HSV2), *C. pneumoniae* and *H. pylori*. The invention also encompasses a method for characterizing an individual's risk profile of developing a future cardiovascular disorder or cardiovascular event associated with atherosclerotic disease, comprising determining the number of seropositive responses to a group of pathogens (pathogen burden) that have been associated with the presence of atherosclerosis and/or clinical events related to atherosclerosis, comparing the pathogen burden to establish a first risk value, obtaining a level of a cholesterol or C-reactive protein (CRP) in the individual, comparing the level of the CRP to a second predetermined CRP value to establish a second risk value, and characterizing the individual's risk profile of developing the cardiovascular disorder based upon the combination of the first risk value and the second risk value, wherein the combination of the first risk value and second risk value establishes a third risk value different from the first and second risk values. The first predetermined value may be pathogen burden and the comparison step may be determining in which of the predetermined marker level ranges the individual's level falls. The comparison may also involve the determined CRP level of the individual.

The invention also contemplates kits comprising assays for measuring pathogen burden, that conveys information as to the susceptibility to the development of atherosclerosis and/or its complications selected from the group consisting of selected from the group including, but not limited to, cytomegalovirus (CMV), hepatitis A virus (HAV), herpes simplex virus type 1 (HSV1), HSV type 2 (hESV2), *C. pneumoniae* and *H. pylori*.

The invention, having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

We claim:

1. A method for determining a decreased risk of an individual for developing coronary artery disease (CAD), comprising:
    obtaining a plasma sample from the individual;
    measuring a plasma level of human Heat Shock Protein 70 (hHSP70) in the sample; and,
    determining if the plasma level of hHSP70 in the sample is greater than 0.5 ng/ml,
    wherein if the plasma level of hHSP70 in the sample is greater than 0.5 ng/ml, the individual has a decreased risk for developing CAD.

2. A method for determining an increased risk of an individual for developing coronary artery disease (CAD), comprising:
    obtaining a plasma sample from the individual;
    measuring a plasma level of human Heat Shock Protein 70 (hHSP70) in the sample; and,
    determining if the plasma level of hHSP70 in the sample is less than 0.5 ng/ml,
    wherein if the plasma level of hHSP70 in the sample is less than 0.5 ng/ml, the individual has an increased risk for developing CAD.

3. The method of claim 2, further comprising
    determining if anti-human-HSP60 antibodies are present in the plasma sample,
    wherein if anti-human-HSP60 antibodies are present in the plasma sample, the individual has an increased risk for developing CAD.

4. The method of claim 2, further comprising
    determining a plasma level of cholesterol in the sample,
    comparing the plasma level of cholesterol in the sample with a predetermined plasma level indicative of an increased risk for developing CAD,
    wherein if the plasma level of cholesterol in the sample is higher than the predetermined plasma level indicative of an increased risk for developing CAD, the individual has an increased risk for developing CAD.

5. The method of claim 2, further comprising
    determining a plasma level of C-reactive protein (CRP) in the sample, and comparing the plasma level of CRP in the sample with a predetermined plasma level indicative of an increased risk for developing CAD,
wherein if the plasma level of CRP in the sample is higher than the predetermined plasma level indicative of an increased risk for developing CAD, the individual has an increased risk for developing CAD.

* * * * *